United States Patent [19]

Sato et al.

[11] 4,368,204

[45] Jan. 11, 1983

[54] NUTRITION COMPOSITION FOR PEDIATRICS

[75] Inventors: Hiroshi Sato; Shohei Ogoshi, both of Chiba; Goro Inoue, Tokushima, all of Japan

[73] Assignee: Ajinomoto Company Incorporated, Tokyo, Japan

[21] Appl. No.: 232,256

[22] Filed: Feb. 6, 1981

[30] Foreign Application Priority Data

Feb. 8, 1980 [JP] Japan .................................. 55-14428

[51] Int. Cl.³ .................... A61K 31/40; A61K 31/195
[52] U.S. Cl. ..................................... 424/274; 424/319
[58] Field of Search ............................... 424/274, 319

[56] References Cited

U.S. PATENT DOCUMENTS 4,144,357 3/1979 Mohammed ......................... 426/96

FOREIGN PATENT DOCUMENTS 2654820 8/1978 Fed. Rep. of Germany.
1371535 10/1974 United Kingdom.

OTHER PUBLICATIONS

Physicians Desk Ref. 27th Ed. (1973) pp. 502, 503, 1420, 1421.
Merck Index, 9th Ed., 1976, Entry 193.

Primary Examiner—Stanley J. Friedman
Attorney, Agent, or Firm—Oblon, Fisher, Spivak, McClelland & Maier

[57] ABSTRACT

A nutritional composition for pediatrics having specified amino acids and amounts thereof is disclosed.

9 Claims, No Drawings

NUTRITION COMPOSITION FOR PEDIATRICS

BACKGROUND OF THE INVENTION

1. Field of the Invention

The present invention relates to a novel nutritional composition for pediatric use.

2. Description of the Prior Art

Elemental diet compositions, comprising amino acids, carbohydrates such as mono- and oligosaccharides, fats, vitamins, minerals, and additives such as preservatives and emulsifiers have been proposed for the nutrition of children in special circumstances.

However, currently available manufactured elemental diet compositions are not always suitable for children having various conditions or illnesses that normally call for the use of such compositions in adults.

For example, irregular or poor metabolism of amino acids can often occur in a child, particularly in a sick or weak child. In such cases, a nutritional composition that varies in the composition and concentration of amino acids present, as in known manufactured compositions, may be ineffective. Therefore, known manufactured compositions are sometimes unable to satisfy the nutritional requirements of children suffering from these conditions.

SUMMARY OF THE INVENTION

Accordingly, it is an object of this invention to provide an elemental nutritional composition that satisfies the nutritional requirements of children.

It is another object of the invention to provide an elemental nutritional composition having a balanced amino acid content suitable for the nutritional requirements of children.

These and other objects of the invention which will hereinafter become more readily apparent have been accomplished by providing a nutritional composition for pediatrics comprising amino acids wherein the following amino acids are present in the indicated amounts:

| Amino Acid | % by Weight of Total Amino Acids |
|---|---|
| L-isoleucine | 4.50 to 6.08 |
| L-leucine | 8.70 to 11.78 |
| L-lysine | 6.58 to 8.90 |
| L-methionine | 1.38 to 1.86 |
| L-cysteine | 1.87 to 2.53 |
| L-phenylalanine | 2.69 to 3.63 |
| L-tyrosine | 3.79 to 5.13 |
| L-threonine | 4.30 to 5.82 |
| L-tryptophan | 1.62 to 2.19 |
| L-valine | 4.65 to 6.29 |
| L-histidine | 2.43 to 3.29 |
| L-alanine | 8.32 to 11.26 |
| L-arginine | 6.00 to 8.12 |
| L-aspartic acid | 3.62 to 4.90 |
| L-glutamic acid | 6.47 to 8.76 |
| glycine | 1.96 to 2.66 |
| L-proline | 8.46 to 11.44 |
| L-serine | 7.66 to 10.36 |
| Total | 100 |

DESCRIPTION OF THE PREFERRED EMBODIMENTS

The inventors have investigated the nutritional requirements of children up to about ten years of age, particularly from neonate to about six years of age, and have completed the present invention based on these findings.

As a result of these studies, the inventors have discovered that the nutritional requirements of children are provided for by a nutritional composition for pediatrics comprising amino acids wherein the following amino acids are present in the indicated amounts:

| Amino Acid | % by Weight of Total Amino Acids |
|---|---|
| L-isoleucine | 4.50 to 6.08 |
| L-leucine | 8.70 to 11.78 |
| L-lysine | 6.58 to 8.90 |
| L-methionine | 1.38 to 1.86 |
| L-cysteine | 1.87 to 2.53 |
| L-phenylalanine | 2.69 to 3.63 |
| L-tyrosine | 3.79 to 5.13 |
| L-threonine | 4.30 to 5.82 |
| L-tryptophan | 1.62 to 2.19 |
| L valine | 4.65 to 6.29 |
| L-histidine | 2.43 to 3.29 |
| L-alanine | 8.32 to 11.26 |
| L-arginine | 6.00 to 8.12 |
| L-aspartic acid | 3.62 to 4.90 |
| L-glutamic acid | 6.47 to 8.76 |
| glycine | 1.96 to 2.66 |
| L-proline | 8.46 to 11.44 |
| L-serine | 7.66 to 10.36 |
| Total | 100 |

In the composition listed above, values for weights of the above-mentioned amino acids are indicated in the free form. However, derivatives or adducts of amino acids which can be metabolized to amino acids in the human body can also be used.

For example, suitable derivatives of amino acids include amine salts with mineral acids, such as hydrochloric acid, or organic acids; carboxylic acid metal salts, such as sodium, potassium, calcium, and magnesium salts; peptides; N-acylated amino acids; and hydrates. For example, amino acids such as lysine, cysteine, histidine, and arginine can be used in the form of a hydrochloric or acetic acid salt. Tyrosine can be used as the ethyl ester hydrochloride or N-acetylated derivative, and aspartic acid can be used as a metal salt, such as a potassium or magnesium salt.

When derivatives of amino acids are used, the required weight of each derivative can be easily calculated from the molecular weights of the derivative and the free forms as is well known in the art.

The total amino acid content in the composition of the present invention may be from about 5 to about 20% of the total weight of the composition.

Various combinations of additional ingredients may be used in the composition of the invention along with the indicated amounts of amino acids. For example, dextrin may be employed as the carbohydrate. Mono- and oligosaccharides may also be employed. The carbohydrate content of the composition is usually about 75 to 85%, but can be higher, if necessary.

Various plant oils, such as corn, soybean, and cotton seed oil, can be employed as fats with the present invention. When a low amount of fat, for example, about 2 to 4% by weight, is used, the solubility and emulsifiability of the composition are improved, and the occurrence of diarrhea in patients sensitive to fats is lessened.

Vitamins in many forms are also suitable for use in the present invention. Some examples include vitamin A as retinole acetate, vitamin $B_1$ as thiamine hydrochloride, vitamin $B_2$ as riboflavine sodium phosphate, vitamin $B_6$ is pyridoxine hydrochloride, vitamin $B_{12}$ as cyanocobalamin, vitamin C as ascorbic acid, vitamin $D_2$ as ergocalciferol, vitamin E as tocopherol acetate, and vitamin $K_1$ as phytonadione. Also suitable are calcium pantothenic acid, nicotinamide, biotin, folic acid, and choline bitartarate, among others.

Generally, about 50 to 100 mg of vitamins are present in 80 g of the nutritional composition, and as such, the concentration of vitamins is about 0.1% by weight.

Particularly useful are compositions containing vitamin C and vitamin $D_2$ in amounts greater than the amounts presently used in elemental diets in view of the growth requirements of children. For example, about 20 to 40 mg of ascorbic acid or about 5 to 15 µg of ergocalciferol is desirably employed per 80 g of the nutritional composition.

Minerals may also be employed in the nutritional composition. Minerals in suitable form include iron as gluconic acid iron salt dihydrate, copper as cupric sulfate pentahydrate, manganese as manganese sulfate pentahydrate, zinc as zinc sulfate heptahydrate, potassium as potassium iodide or potassium chloride, sodium as sodium citrate dihydrate, calcium as calcium glycerophosphate, magnesium as magnesium sulfate heptahydrate, and others. About 3,000 to 5,000 mg of minerals are employed per 80 g of the nutritional composition, and, as such, the concentration of minerals is about 2 to 8% by weight.

Particularly useful are compositions containing iron and calcium in amounts greater than those presently employed in known elemental nutritional diets, in view of the growth requirements of children. For example, about 30 to 60 mg of gluconic acid iron salt dihydrate or 1,400 to 2,000 mg of calcium glycerophosphate may be employed per 80 g of the nutritional composition.

When the nutritional composition of the present invention is manufactured as a finished good, preservatives, such as potassium sorbate, and emulsifiers, such as polysorbate and soy phosphatides, can be added, thereby reducing the ability of the composition to support growth of contaminating microoogransims while in powder form or in solution and making the dissolution or emulsification of the composition easier.

When the nutritional composition produced in accordance with the present invention is administered to a small child, emulsified and homogenized material is preferred for ease of administration and digestion.

The nutritional composition of the present invention is widely useful, since it can be administered either by intestinal intubation or oral ingestion. A non-toxic carrier suitable for human use, such as water, milk, or an aqueous solution or suspension of various non-toxic organic or inorganic substances, may be used as an aid in the administration of the composition.

When the composition is administered orally, it is employed in the form of a paste or solution and is administered together with milk. Further, the nutritional composition may contain flavors, seasonings, acidophilus-containing-drinks, or other materials to increase pleasure of eating and drinking.

When the nutritional composition is administered by intestinal intubation, it may be used as a water solution or mixture, e.g., with warm water, in the concentration of, for example, about 5 to 40% (w/v).

Products according to the present invention can be used widely for the nutrition of sick children. Examples include controlled nutrition before or after a surgical operation and improvement of nutrition in cases of poor digestion or malabsorption.

Having generally described the invention, a more complete understanding can be obtained by reference to certain specific examples, which are provided herein for purposes of illustration only and are not intended to be limiting unless otherwise specified.

EXAMPLES

The following substances were homogeneously mixed in the powder state:

| Substance | Weight |
| --- | --- |
| L-histidine monohydrochloride monohydrate | 0.380 g |
| L-isoleucine | 0.519 g |
| L-leucine | 1.004 g |
| L-lysine monohydrochloride | 0.949 g |
| L-methionine | 0.159 g |
| L-cysteine hydrochloride monohydrate | 0.313 g |
| L-phenylalanine | 0.310 g |
| N—acetyl-L-tyrosine | 0.538 g |
| L-threonine | 0.496 g |
| L-tryptophan | 0.186 g |
| L-valine | 0.537 g |
| L-alanine | 0.960 g |
| L-arginine | 0.693 g |
| Mixture of di-L-aspartic acid monomagnesium and L-aspartic acid monopotassium in the ratio 1:1 | 0.547 g |
| glycine | 0.227 g |
| L-glutamic acid | 0.747 g |
| L-proline | 0.976 g |
| L-serine | 0.883 g |
| dextrin | 62.88 g |
| soybean oil | 2.400 g |
| retinol acetate | 0.372 mg |
| thiamine hydrochloride | 0.323 mg |
| riboflavine sodium phosphate | 0.427 mg |
| pyridoxine hydrochloride | 0.445 mg |
| cyanocobalamin | 1.200 µg |
| ascorbic acid | 28.600 mg |
| ergocalciferol | 8.532 µg |
| tocopherol acetate | 5.507 mg |
| phytonadione | 14.667 mg |
| calcium pantothenic acid | 1.987 mg |
| nicotinamide | 3.667 mg |
| biotin | 65.333 µg |
| folic acid | 73.333 µg |
| choline bitartarate | 29.880 mg |
| gluconic acid iron salt dihydrate | 43.97 mg |
| cupric sulfate pentahydrate | 1.373 mg |
| manganese sulfate pentahydrate | 2.173 mg |
| zinc sulfate heptahydrate | 214.7 mg |
| potassium sorbate | 120. mg |
| "polysorbate 80" | 117.6 mg |
| soy phosphatide | 16.8 mg |

The above mixture was converted to a paste with water or dissolved in water for oral administration. Eighty grams of the above mixture was dissolved in warm water to give 300 ml of solution (26.7% (w/v); specific gravity, 1.09) to form the standard solution used for administration by intestinal intubation. Further mixtures or solutions having several concentrations in the range from 5 to 40% (w/v) were produced for administration through a fine catheter into the duodenum or jejunum of a child.

Having now fully described the invention, it will be apparent to one of ordinary skill in the art that many changes and modifications can be made thereto without departing from the spirit or scope of the invention as set forth herein.

What we claim is:

1. A nutritional composition comprising: amino acids, wherein the following amino acids are present in the indicated amounts:

| Amino Acid | % by Weight of Total Amino Acids |
| --- | --- |
| L-isoleucine | 4.50 to 6.08 |
| L-leucine | 8.70 to 11.78 |
| L-lysine | 6.58 to 8.90 |
| L-methionine | 1.38 to 1.86 |
| L-cysteine | 1.87 to 2.53 |
| L-phenylalanine | 2.69 to 3.63 |
| L-tyrosine | 3.79 to 5.13 |
| L-threonine | 4.30 to 5.82 |
| L-tryptophan | 1.62 to 2.19 |
| L-valine | 4.65 to 6.29 |
| L-histidine | 2.43 to 3.29 |
| L-alanine | 8.32 to 11.26 |
| L-arginine | 6.00 to 8.12 |
| L-aspartic acid | 3.62 to 4.90 |
| L-glutamic acid | 6.47 to 8.76 |
| glycine | 1.96 to 2.66 |
| L-proline | 8.46 to 11.44 |
| L-serine | 7.66 to 10.36 |
| Total | 100 |

2. A nutritional composition as described in claim 1, wherein at least one amino acid of said amino acids is present as a derivative or adduct of said amino acid which can be metabolized in the human body to said amino acid.

3. A nutritional composition as described in claim 2, wherein said derivative or adduct is an amine salt of an amino acid with a mineral or organic acid, a carboxylic acid metal salt of an amino acid, a peptide, an N-acylated amino acid, or a hydrate of an amino acid or derivative of adduct.

4. A nutritional composition as described in claim 1 or 2, wherein said amino acids make up 5 to 20% by weight of total solids present in said composition.

5. A nutritional composition as described in claim 1 or 2, wherein said composition additionally contains a plant oil, a vitamin, a mineral, a preservative, an emusifier, or a flavoring agent.

6. A nutritional composition as described in claim 1 or 2, wherein said composition also comprises a nontoxic carrier.

7. A nutritional composition as described in claim 6, wherein said carrier is water or an aqueous solution or suspension.

8. A method of fulfilling the nutritional requirements of a child, comprising the step of:
administering to a human child the nutritional composition of claim 1, 2, or 6.

9. The method of claim 8, wherein said composition is administered orally or by intestinal intubation.

* * * * *